United States Patent [19]
Erskine

[11] Patent Number: 6,090,078
[45] Date of Patent: *Jul. 18, 2000

[54] DAMPENING DEVICES AND METHODS FOR NEEDLE RETRACTING SAFETY VASCULAR ACCESS DEVICES

[75] Inventor: Timothy J. Erskine, Sandy, Utah

[73] Assignee: Becton, Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/941,450

[22] Filed: Sep. 30, 1997

[51] Int. Cl.<sup>7</sup> ...................................... A61M 5/32
[52] U.S. Cl. ........................... 604/198; 604/230; 128/919
[58] Field of Search ..................... 604/110, 122, 604/126, 162, 164–166, 168, 171, 221–222, 226, 230–231, 240, 243, 263, 195, 198; 128/919

[56] References Cited

U.S. PATENT DOCUMENTS

| | | | |
|---|---|---|---|
| 2,629,376 | 2/1953 | Gallice et al. | 604/222 |
| 2,756,748 | 7/1956 | Ferguson . | |
| 3,581,956 | 6/1971 | Reid . | |
| 4,813,937 | 3/1989 | Vaillancourt | 604/131 |
| 4,863,072 | 9/1989 | Perler . | |
| 4,955,869 | 9/1990 | Bin | 604/195 |
| 5,047,016 | 9/1991 | Dolgin et al. | 604/110 |
| 5,064,419 | 11/1991 | Gaarde | 604/195 |
| 5,090,961 | 2/1992 | Maruzik et al. | 604/110 |
| 5,171,300 | 12/1992 | Blake, III et al. | 604/110 |
| 5,215,533 | 6/1993 | Robb | 604/195 |
| 5,263,933 | 11/1993 | Novacek et al. | 604/110 |
| 5,330,430 | 7/1994 | Sullivan | 604/134 |
| 5,405,327 | 4/1995 | Chen | 604/110 |
| 5,407,436 | 4/1995 | Toft et al. | 604/195 |
| 5,501,675 | 3/1996 | Erskine | 604/263 |
| 5,562,629 | 10/1996 | Haughton et al. | 604/158 |
| 5,575,777 | 11/1996 | Cover et al. | 604/198 |
| 5,702,367 | 12/1997 | Cover et al. | 604/109 |
| 5,785,687 | 7/1998 | Saito | 604/110 |
| 5,797,880 | 8/1998 | Erskine | 604/110 |
| 5,817,058 | 10/1998 | Shaw | 604/110 |
| 5,827,221 | 10/1998 | Phelps | 604/51 |
| 5,843,034 | 12/1998 | Redfern et al. | 604/110 |
| 5,865,803 | 2/1999 | Major | 604/122 |

*Primary Examiner*—Wynn Wood Coggins
*Assistant Examiner*—LoAn H. Thanh
*Attorney, Agent, or Firm*—Eric M. Lee

[57] ABSTRACT

Devices and methods for slowing down or dampening the retraction velocity of an introducer needle used in connection with needle retracting safety vascular access devices. The devices and methods prevent splattering or dripping of blood caused by an introducer needle that retracts too quickly. The dampening devices can be easily modified to regulate the amount of dampening desired and can be retrofitted to existing vascular access devices designs.

3 Claims, 10 Drawing Sheets

DAMPENING DEVICES AND METHODS FOR NEEDLE RETRACTING SAFETY VASCULAR ACCESS DEVICES

1. THE FIELD OF THE INVENTION

The present invention relates to needle retracting safety vascular access devices. More particularly, the present invention relates to devices that dampen the retraction velocity of needles used in connection with needle retracting safety vascular access devices, thus preventing blood splattering or dripping as the needle retracts into the housing.

2. BACKGROUND

During medical treatment, patients often require medication, blood, or fluids. The most efficient way of administering these substances is by depositing them directly into the patient's blood stream where the circulatory system quickly directs the substance to the target tissue or organ. Administering a substance directly into a patient's blood stream is most commonly accomplished by injection with a conventional needle and syringe. During the course of treatment, however, a patient will often require repeated or continuous doses of medications. It will be appreciated that repeated injections with conventional syringes can damage blood vessels and cause significant discomfort to the patient.

Therefore, when a patient requires repeated doses of medication or other substances, catheters are commonly used in the health care profession. In one common configuration, a catheter comprises a catheter adaptor and a hollow tubular cannula. The catheter adaptor and the catheter cannula are attached end-to-end. The catheter adaptor and cannula are usually constructed from a single mold such that a continuous fluid flow opening extends from the catheter adaptor to the catheter cannula. When the catheter is in use, the hollow tubular cannula is partially inserted into the patient's blood vessel, while the catheter adaptor remains outside where it can be accessed by medical personnel. A medication container is securely attached to the catheter adaptor. The medication flows through the catheter adaptor and cannula via the continuous fluid flow opening and directly into the patient's blood vessel. As such, the patient receives a continuous supply of medication without repeated injections with conventional needles and syringes.

Typically, a vascular access device is used to insert a catheter within a patient's blood vessel. A vascular access device generally comprises a housing, an introducer needle, and a catheter. The housing is used to grip the vascular access device during catheter insertion. The introducer needle is attached to the end of the housing and used to pierce the patient's skin and access the blood vessel. The catheter fits concentrically over the introducer needle and is held in place by friction engagement between a catheter adaptor and the housing. The relative lengths of the introducer needle and the catheter cannula are such that the tip of the introducer needle extends beyond the end of the catheter cannula when the catheter adaptor is attached to the housing.

In use, a clinician pierces the patient's skin with the introducer needle and locates the patient's blood vessel. Once the introducer needle is inserted into the patient's blood vessel, the patient's blood pressure causes blood to flow into the introducer needle. This "flashback" blood is allowed to exit into a chamber positioned within the housing. The chamber and housing are usually made of a clear or opaque material so that the clinician can see the flashback blood entering the chamber. Flashback blood in the chamber alerts the clinician that the blood vessel has been successfully punctured. With the introducer needle in the patient's blood vessel, the clinician detaches the catheter adaptor from the housing. The catheter cannula is then inserted into the patient's blood vessel by sliding the catheter cannula along the introducer needle until the desired length of the cannula is within the blood vessel. While holding the catheter in place, the introducer needle is removed by slowing pulling back on the housing leaving the catheter cannula within the patient's blood vessel.

It will be appreciated that the introducer needle is contaminated with the patient's blood and any blood borne diseases, such as HIV and hepatitis, the patient may carry. Exposed introducer needles, therefore, pose a health hazard to clinicians and other patients. To lessen the risk of accidental needle punctures or blood exposure, some vascular access devises are designed with spring retracting needles. Once the cannula is positioned within the patient's blood vessel, the clinician disengages a locking mechanism thus allowing the spring to propel the needle into the housing of the vascular access device. The housing completely encloses the needle, protecting the clinician from accidental needle punctures.

While spring retracted needle designs significantly cut down on accidental needle punctures, some improvements to the designs could be made. It will be appreciated that as the needle retracts, some blood will adhere to the needle through normal surface tension. Usually, this small amount of blood does not pose a threat to clinicians because it becomes enclosed by the housing. If the needle retracts too fast, however, blood on the needle may break the surface tension and splatter or drip on the patient or clinician. The potentially contaminated blood posses a serious health threat to the clinician and other medical personnel.

From the foregoing, it will be appreciated that it would be an advancement in the art to provide devices for slowing down or dampening the velocity of the needle as it retracts into the housing of the vascular access device.

It would also be an advancement if the dampening devices prevented blood from splattering or dripping during needle retraction.

It would be yet another advancement in the art if the dampening devices could be regulated to provide different degrees of dampening.

It would be a further advancement in the art if existing vascular access devices could be retrofit with the dampening devices.

Such dampening devices and methods are disclosed and claimed herein.

3. BRIEF SUMMARY AND OBJECTS OF THE INVENTION

The present invention relates to dampening devices and methods that dampen the retraction velocity of needles used in connection with semi-automatic needle retracting vascular access devices. These devices prevent splattering or dripping of blood during needle retraction. In addition, the dampening devices of the present invention can be modified to regulate the amount of dampening and can be retrofit to existing vascular access devices.

In one embodiment, a needle retracting safety vascular access device comprises a housing having a housing cavity. An introducer needle is positioned with its proximal end residing outside the housing and its distal end disposed within the housing cavity. As used herein, the term proximal means the end of the device furthest from the practitioner, and the term distal means the portion of the device closest to the practitioner. The introducer needle is placed in communication with a hub which holds the needle in place during insertion and retraction. The hub, in turn, is in communication with a spring retraction mechanism. A dampening device comprising a collapsible bladder is disposed within the housing cavity and positioned at the distal end of the needle. The distal end of the bladder has a bladder vent which allows ambient air in the bladder to exit. As the needle begins to retract into the housing cavity, the needle contacts the bladder which is filled with ambient air. The ambient air filled bladder dampens the velocity of the needle. Air is expelled through the bladder vent in a controlled manner by the pressure of the spring, thus allowing the needle to likewise retract in a controlled fashion.

In a second embodiment, a needle retracting safety vascular access device comprises a housing having a housing cavity. An introducer needle is positioned with its proximal end residing outside the housing and its distal end disposed within the housing cavity. The introducer needle is placed in communication with a hub which holds the needle in place during insertion and retraction. The hub, in turn, is in communication with a spring retraction mechanism. A dampening device comprising a piston is disposed within the housing cavity near the distal end of the needle. The piston is in communication with the needle so that it retracts concurrently with the needle during retraction. The piston has at least one wiping flange configured around the piston. The wiping flange creates a seal between the piston and the housing cavity. The housing additionally has at least one longitudinal vent groove carved into the housing cavity. As the needle and the piston move distally through the housing cavity during retraction, ambient air in the housing cavity is compressed by the piston thereby dampening the velocity of the needle. Air is expelled in a controlled manner through the longitudinal vent groove by the pressure of the spring, thus allowing the needle to likewise retract in a controlled fashion.

In a third embodiment, once again a needle retracting safety vascular access device comprises a housing having a housing cavity. The distal end of the housing also has a housing vent. An introducer needle is positioned with its proximal end residing outside the housing and its distal end disposed within the housing cavity. The introducer needle is placed in communication with a hub which holds the needle in place during insertion and retraction. The hub, in turn, is in communication with a spring retraction mechanism. A dampening device comprising a piston is disposed within the housing cavity and positioned at the distal end of the needle. The piston is in communication with the needle so that it retracts concurrently with the needle during needle retraction. The piston comprises a circumferential groove. The circumferential groove is completely filled with a viscous material so that it is in contact with the housing. As the needle and piston move distally during retraction, the resistance of the viscous material against the housing dampens the velocity of the needle, thus allowing the needle to retract in a slow and controlled fashion. Ambient air compressed during retraction is expelled out of the housing vent.

In a fourth embodiment, a needle retracting safety vascular access device comprises a housing having a housing cavity. An introducer needle is positioned with its proximal end residing outside the housing and its distal end disposed within the housing cavity. The distal end of the introducer needle has at least one needle flange. The introducer needle is placed in communication with a hub which holds the needle in place during insertion and retraction. The hub, in turn, is in communication with a spring retraction mechanism. A dampening member is disposed within the housing cavity and positioned at the distal end of the needle. The dampening member comprises at least one track. Disposed within the track is a viscous material, such as silicone. As the needle move distally during retraction, the flange slides down the track of the dampening member. The resistance of the flange against the viscous material disposed within the track dampens the velocity of the needle, thus allowing the needle to retract in a slow and controlled fashion.

In fifth embodiment, a needle retracting safety vascular access device comprises a housing having a housing cavity. An introducer needle is positioned with its proximal end residing outside the housing and its distal end disposed within the housing cavity. The introducer needle is placed in communication with a hub which holds the needle in place during insertion and retraction. The hub, in turn, is in communication with a coiled spring retraction mechanism. Disposed within the housing cavity is at least one spring compression node positioned distally of the spring. The node reduces the effective diameter of housing cavity. The spring compression node dampens the velocity of the needle by requiring that each individual coil radially contract before it can advance past the spring compression node and continue through the housing cavity. As each coil of the spring advances past the spring compression node, the hub, and hence introducer needle, is slowly urged distally until the introducer needle is completely within the housing cavity These and other objects and advantages of the present invention will become more fully apparent by examination of the following description of the preferred embodiments and the accompanying drawings.

4. BRIEF DESCRIPTION OF THE DRAWINGS

The appended drawings will provide a better description of the invention briefly described above. These drawings only provide information concerning typical embodiments of the invention and are not limiting in scope.

5. DETAILED DESCRIPTION OF THE PREFERRED EMBODIMENTS

Figure 1:
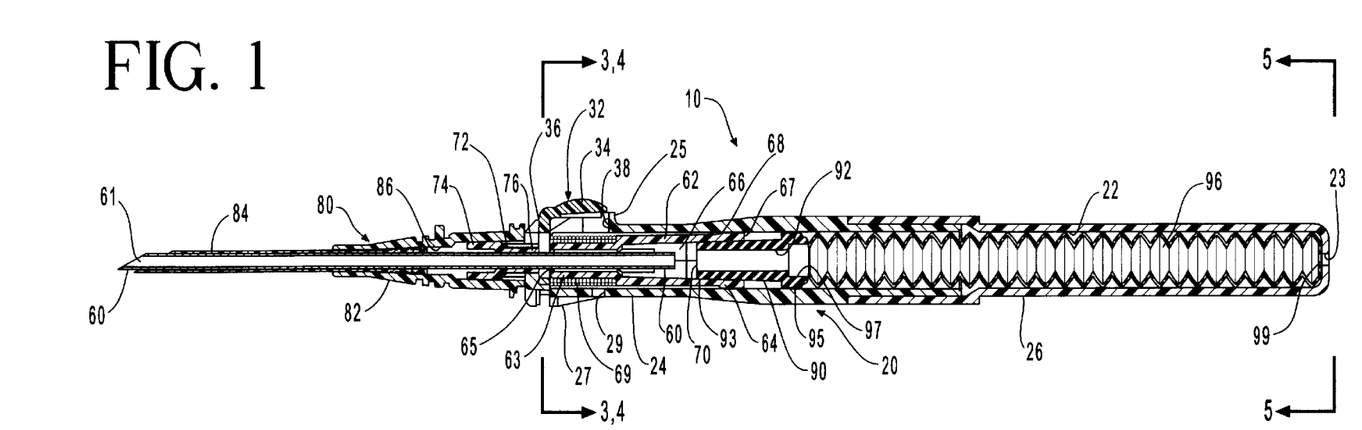
FIG. 1 is a longitudinal cross sectional view of the collapsible bladder dampening device embodiment of the present invention showing the introducer needle prior to retraction and the collapsible bladder fully expanded.

Reference is now made to the figures wherein like parts are referred to by like numerals throughout. With particular reference to FIG. 1, the present invention is a vascular access device 10 shown prior to needle retraction. Vascular access device 10 generally comprises a housing 20 having a cylindrical interior housing cavity 22, a catheter 80, a hollow introducer needle 60, means for retracting introducer needle 60 into housing cavity 22 after use, and means for dampening the velocity and force at which the needle is retracted in housing cavity 22.

Housing 20 is cylindrically shaped and generally used to grip vascular access device 10. Housing 20 has a proximal housing 24 near introducer needle 60 and a distal housing 26. Proximal housing 24 has a generally cylindrical grease port 29. Housing 20 is typically made of a rigid plastic material. For reasons discussed in detail below, housing 20 is preferably made of a clear or opaque material so that the clinician can observe flashback blood entering housing 20 and a flashback chamber 66. Distal housing 26 is likewise constructed of a rigid material and has a housing vent 23. Distal housing 26 may be made from a unitary mold with proximal housing 24 or, as illustrated in FIG. 1, molded separately and secured to proximal housing 24 by, for example, adhesive means or other means well known in the art.

Figure 2:
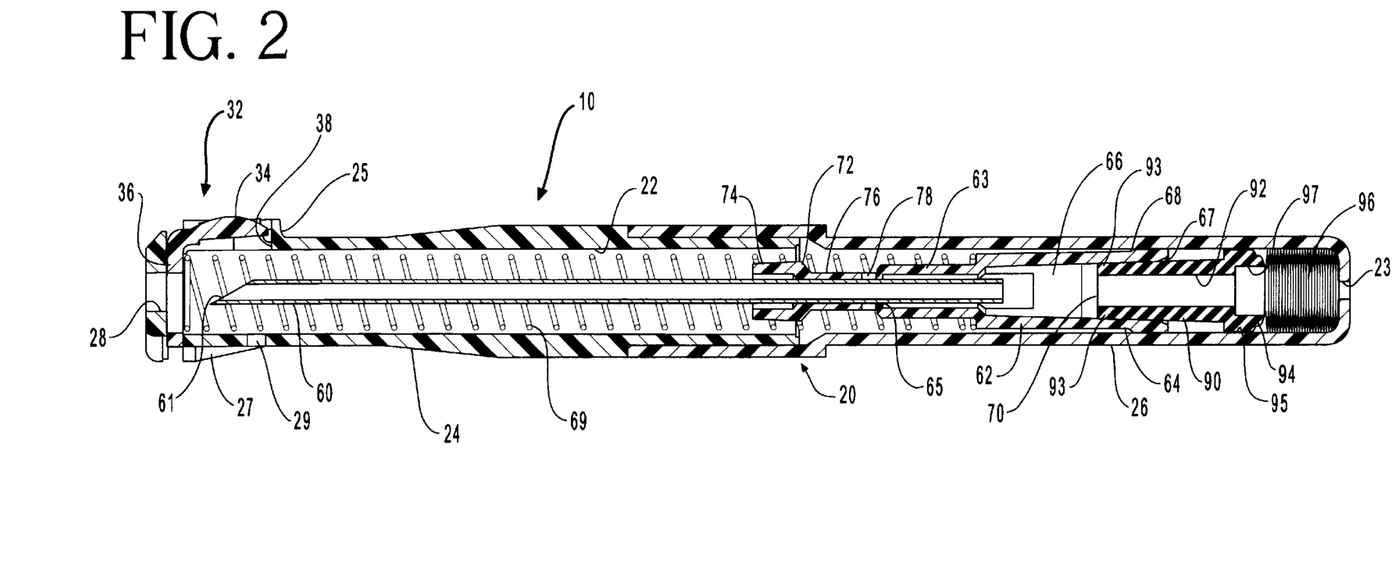
FIG. 2 is a longitudinal cross sectional view of the collapsible bladder dampening device embodiment of the present invention showing the introducer needle after retraction and the collapsible bladder fully compressed.
Figure 3:
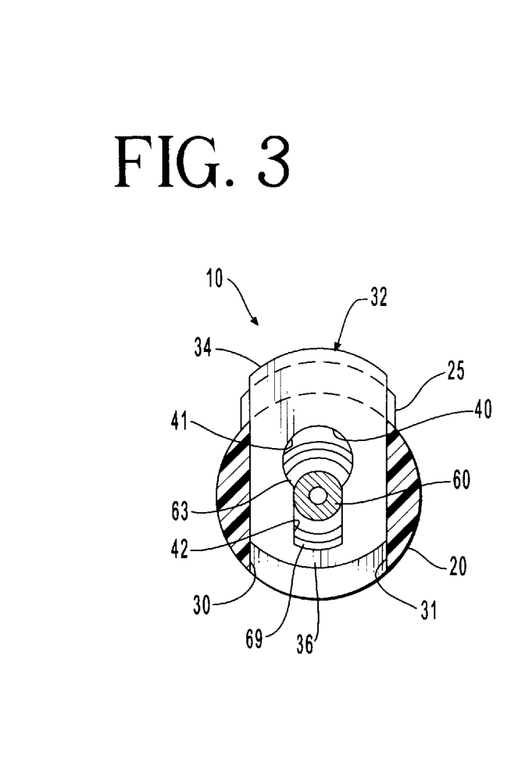
FIG. 3 is a cross sectional view of the introducer needle locking mechanism of the present invention shown in a locked position.
Figure 4:
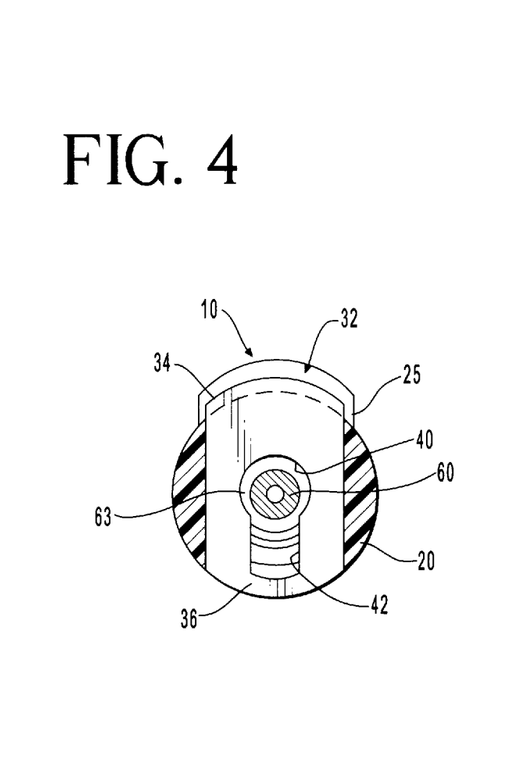
FIG. 4 is a cross sectional view of the introducer needle locking mechanism of the present invention shown in an unlocked position.

Housing 20 has a trigger grip 25 and a ramp grip 27. Additionally, proximate housing 24 is tapered near trigger grip 25. Together trigger grip 25, ramp grip 27, and tapered proximal end 24 allow the clinician to tightly and securely grip vascular access device 10. As best illustrated in FIG. 2, proximal housing 24 has a proximal housing aperture 28 which allows introducer needle 60 to enter housing cavity 22 during retraction. As best illustrated in FIGS. 3 and 4, a pair of opposing slots 30 and 31 run transversely and perpendicularly through proximal housing 24. A locking member 32 having a trigger 34 and a perpendicularly attached lock plate 36 is positioned near the proximal housing 24. More specifically, lock plate 36 is slidably received through opposed slots 31 and 32. A trigger recess 38 accommodates trigger 34 when it is depressed to initiate retraction of introducer needle 60. As best illustrated in FIG. 3, lock plate 36 has a keyhole-shaped lock aperture 40. Lock aperture 40, in turn, has a circular aperture portion 41 and a rectangular aperture portion 42.

As illustrated in FIGS. 1 and 2, disposed within housing cavity 22 is a generally cylindrical hollow hub 62. The interior cavity of hub 62 defines flashback chamber 66. Like housing 20, hub 62 is preferably made of a clear or opaque material so that clinicians can observe flashback blood enter hub 62 and flashback chamber 66. As illustrated by FIGS. 1 and 2, hub 62 is sized such that it can travel the entire length of housing cavity 22, from proximal housing 24 to distal housing 26. Hub 62 additionally comprises a proximal hub 63 and a distal hub 64. Proximate hub 63 has a reduced diameter relative to distal hub 64. As best illustrated in FIG. 2, the disparity in relative diameters defines a hub shoulder 68. As shown in FIG. 1, prior to needle retraction, hub shoulder 68 is positioned near proximal housing 24.

The distal end of introducer needle 60 extends through a proximal hub opening 65. Introducer needle 60 is in fluid communication with flashback chamber 66. The outer diameter of introducer needle 60 and the inner diameter of proximal hub opening 65 are dimensioned so that introducer needle 60 is sealingly secured to hub 62. The remainder of introducer needle 60 extends proximally from hub 62 and out housing 20 through needle passage aperture 28. The proximal end of introducer needle 60 has a beveled tip 61.

A coil spring 69, or other resilient member, concentrically fits over introducer needle 60 and proximal hub 63. The diameter of spring 69 is greater than the diameter of proximal hub 63 and circular aperture 41 of lock aperture 40, but smaller than the diameter of distal hub 64. Prior to retraction, spring 69 is compressed between lock plate 36 and hub shoulder 68 of hub 62. It will be appreciated by one skilled in the art that the resilience of the spring or the length of proximal hub 63 may be varied to control the velocity and force with which introducer needle 60 is retracted.

As best illustrated in FIG. 2, securely attached to the distal end of introducer needle 60, but proximal of hub 62, is a generally cylindrical catheter adaptor 72. Catheter adaptor 72 comprises a larger diameter proximal catheter adaptor 74 and a smaller diameter distal catheter adaptor 76. A gap between hub 62 and distal catheter adaptor 76 defines a circumferential groove 78. The width of circumferential groove 78 is approximately equal to or slightly greater than the width of lock plate 36. Distal catheter adaptor 76 is securely fastened to, or molded around, introducer needle 60.

As best illustrated in FIG. 2 and 3, prior to retraction, introducer needle 60 and catheter adaptor 72 extend through circular portion 41 of lock aperture 40 and beyond proximal housing aperture 28. Introducer needle 60 and catheter adaptor 72 are urged to this forward position with locking member 32 initially in a disengaged position. In a disengaged position, lock plate 36 is completely recessed within opposing slots 30 and 31 thereby aligning circular portion 41 of lock aperture 40 with introducer needle 60 and catheter adaptor 72. Introducer needle 60 and catheter adaptor 72 can then be passed through circular portion 41 of lock aperture 40, aligning lock plate 36 with circumferential groove 78. With lock plate 36 and circumferential groove 78 aligned, lock member 32 is raised so that the rectangular portion 42 of lock aperture 40 is positioned within in circumferential groove 78. Because the width of rectangular portion 42 is narrower than the diameter of distal catheter adaptor 76, introducer needle 60 and catheter adaptor 72 are held in a forward position against the force of spring 69.

Catheter 80 is concentrically positioned over introducer needle 60 and proximal catheter adaptor 74. Catheter 80 generally comprises a catheter housing 82 and a hollow tubular cannula 84. Catheter housing 82 and hollow tubular cannula 84 are sealingly coupled and in fluid communication. Catheter housing 82 has a interior circumferential cavity 86. Catheter housing cavity 86 concentrically fits over, and attaches via friction engagement with, proximal catheter adaptor 74. The friction engagement of proximal catheter adaptor 74 against catheter housing cavity 86 securely holds introducer needle 60 during catheter insertion.

Hollow tubular cannula 84 concentrically fits over introducer needle 60. The length of hollow tubular cannula 84 is shorter that the length of introducer needle 60 such that beveled tip 61 extends beyond the proximal end of hollow tubular cannula 84. Thus, during catheter insertion, beveled tip 61 is exposed and available to pierce the patient's skin and blood vessel. If an introducer needle with a mid-needle blood outlet is used, catheter cannula 84 is preferably constructed of a clear or opaque material which permits the clinician to see the flashback blood exiting the mid-needle blood outlet during catheter insertion.

In one embodiment shown in FIGS. 1 and 2, the vascular access device 10 of the present invention has a dampening adaptor 90. Dampening adaptor 90 has cylindrical interior bore 92, a proximal dampening adaptor 93, and a distal dampening adaptor 94. The outer diameter of proximal dampening adaptor 93 is smaller and is sealingly received by the larger inner diameter of a distal hub opening 67. Proximal dampening adaptor 93 is coupled to distal hub opening 67 by friction, adhesive or other engagement well known in the art. The proximal opening of interior bore 92 has an air permeable, but liquid impermeable, plug 70 which allows air displaced in flashback chamber 66 by flashback blood to pass into interior bore 92.

Distal dampening adaptor 94 has a circumferential guide ring 95 with a diameter slightly smaller than the diameter of housing cavity 22 of housing 20. Guide ring 95 keeps dampening adaptor 90 from moving laterally and uncoupling from distal hub opening 67 as introducer needle 60 and hub 62 retract into housing 20. Distal dampening adaptor 94 also has a bladder port 97.

Figure 5:
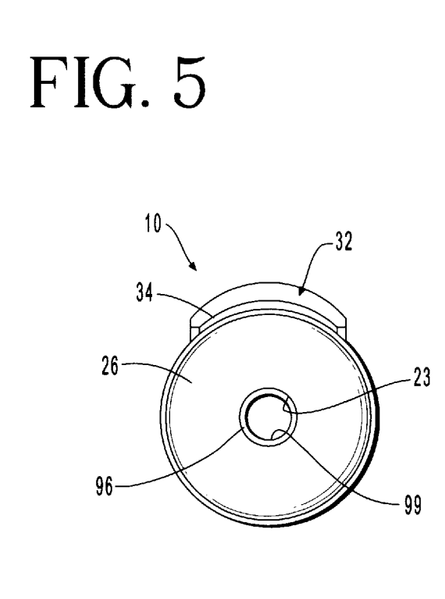
FIG. 5 is a rear view of the housing of the collapsible bladder dampening device embodiment of the present invention showing the housing vent and bladder vent.

A collapsible thin-walled bladder 96 is positioned distally of dampening adaptor 90. When expanded prior to needle retraction as shown in FIG. 1, is filled with ambient air and extends from the dampening adaptor 90 to distal housing 26. As best illustrated in FIG. 5, collapsible bladder 96 is air tight except for a bladder vent 99 at its distal end. The size of bladder vent 99 regulates the amount of dampening collapsible bladder 96 will provide during needle retraction. When properly positioned within the housing cavity 22, bladder vent 99 is aligned with housing vent 23. Bladder 96 is made of a material that allows bladder 96 to retain its fully expanded form without requiring bladder 96 to be connected to dampening adaptor 90. Bladder 96 may, however, be connected to dampening adaptor 90 via bladder port 97. As illustrated in FIG. 2, subsequent to retraction, collapsible bladder 96 is completely compressed in distal housing 26 near housing vent 23.

The force of spring 69 can additionally be dampened using grease port 29 which is in communication with housing cavity 22 and spring 69. High viscous silicone, for example, can be injected through grease port 29 to coat spring 69. The friction of the viscous silicone with housing cavity 22 will slow the velocity and force with which spring 69 retracts introducer needle 60 into housing cavity 22.

In practice, the clinician first punctures the skin with introducer needle 60 and locates the patient's blood vessel. Once introducer needle 60 punctures the blood vessel, blood travels distally through introducer needle 60 displacing air through plug 70 and bore 92. Once passed dampening adaptor 90, air can escape, for example, through the annular spaces between guide ring 95 and housing cavity 22, and out proximal housing aperture 28. The blood will eventually reach flashback chamber 66 alerting the clinician that the blood vessel has been successfully punctured and that introducer needle 60 should not be advanced further. Catheter housing 82 is then uncoupled from catheter adaptor 72 and catheter cannula 84 is advanced into the patient's blood vessel by sliding it along introducer needle 60.

While holding catheter 80 in place, the clinician depresses trigger 34 urging lock plate 36 downwardly and forcing rectangular portion 42 of lock aperture 40 out of circumferential groove 78 until circular portion 41 aligns with catheter adaptor 72. The diameter of catheter adaptor 72 being smaller than the diameter of circular portion 41 no longer opposes the force of spring 69 against lock plate 36 and shoulder 68 of hub 62. Consequently, spring 69 urges hub 62, and hence introducer needle 60, distally into housing cavity 22. Bladder 96 which is filled with ambient air dampens the force of spring 69 and slows down the velocity with which introducer needle 60 is retracted. The force of spring 69 being greater than the opposing force of bladder 96, causes the air to be expelled from bladder vent 99 of bladder 96 and out housing vent 23. Once the air is out of bladder 96, bladder 96 is completely compressed at the rear of distal housing 26 and introducer needle 60 is completely within housing cavity 22. With introducer needle 60 fully retracted, the clinician secures catheter 80 to the patient and connects medication to catheter housing 82 where it is deposited directly into the patient's blood stream.

Figure 6:
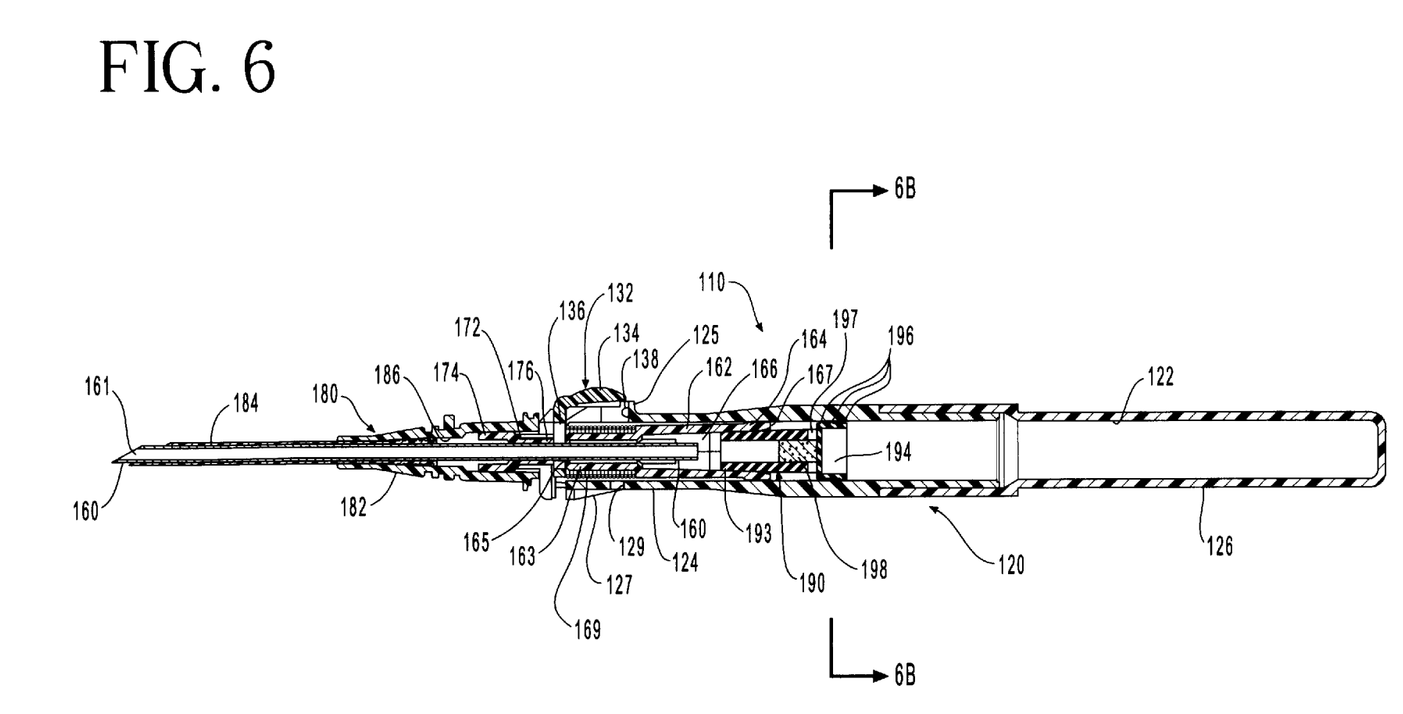
FIG. 6 is a longitudinal cross sectional view of the piston air dampening device embodiment of the present invention showing the introducer needle prior to retraction.
Figure 7:
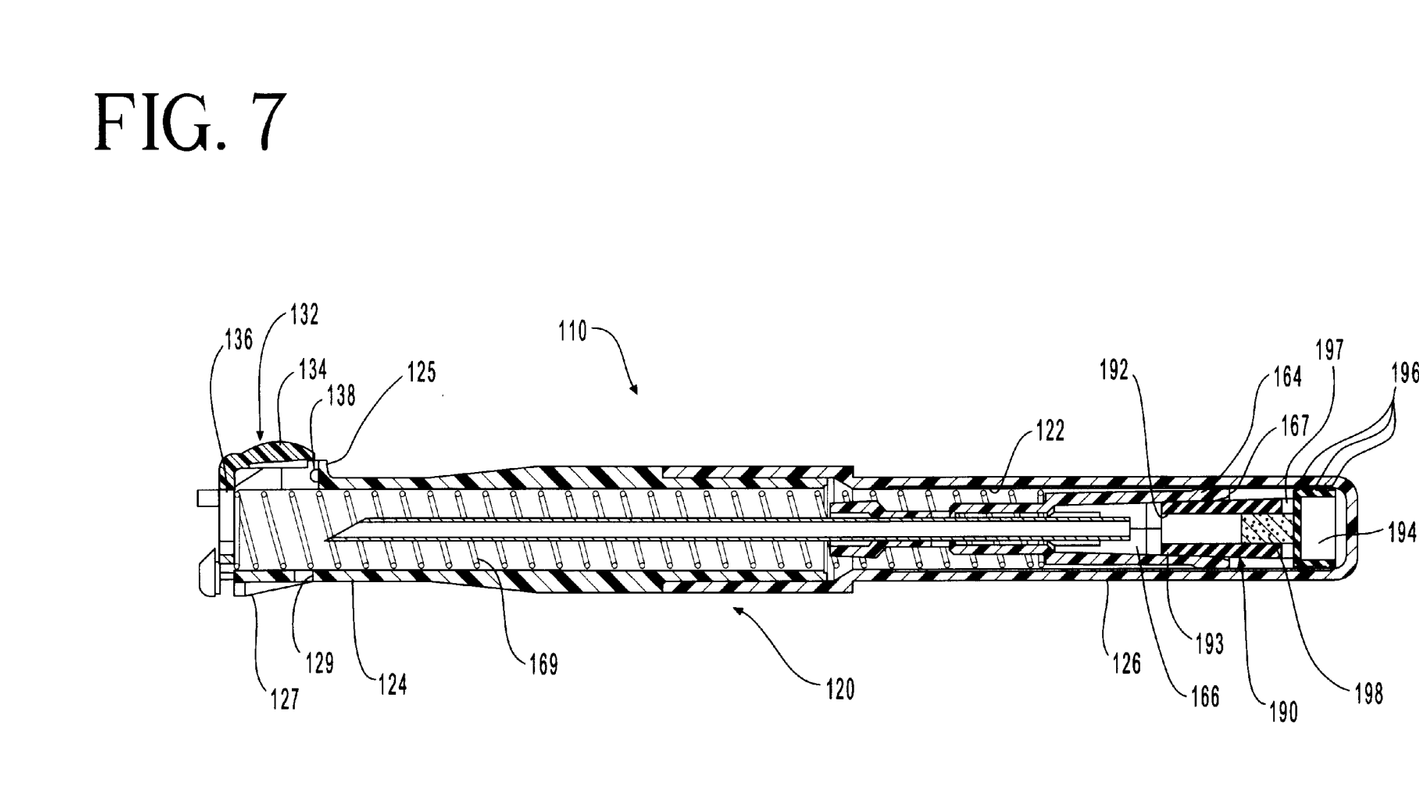
FIG. 7 is a longitudinal cross sectional view of the piston air dampening device embodiment of the present invention showing the introducer needle after retraction.

In a second embodiment the vascular access device operates in the same manner as described above except that a different dampening mechanism is used. Like parts are referred to by like numerals except that in this embodiment they begin with the number "1," indicating the part belongs to the second embodiment. As illustrated in FIGS. 6–7, the vascular access device 110 of the present invention has a dampening adaptor 190. Dampening adaptor 190 has cylindrical interior bore 192, and a proximal dampening adaptor 193. The outer diameter of proximal dampening adaptor 193 is smaller than, and is sealingly received by, the larger inner diameter of distal hub opening 167, placing flashback chamber 166 and dampening adaptor 190 in fluid communication. Proximal dampening adaptor 193 is coupled to distal hub opening 167 by friction, adhesive or other engagement well known in the art.

Figure 6A:
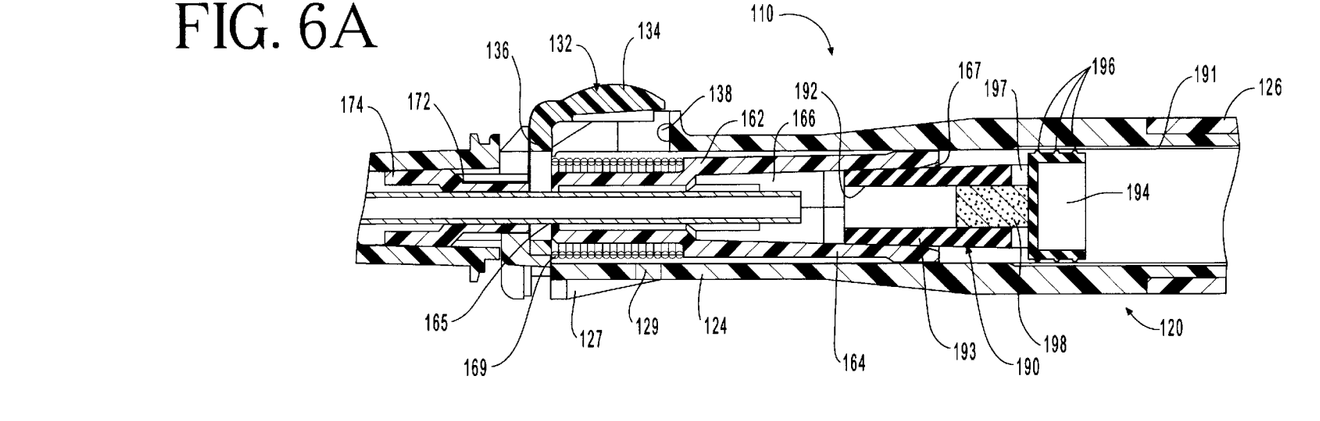
FIG. 6a is a longitudinal cross sectional view of the piston air dampening device embodiment of the present invention showing the wiping flanges.
Figure 6B:
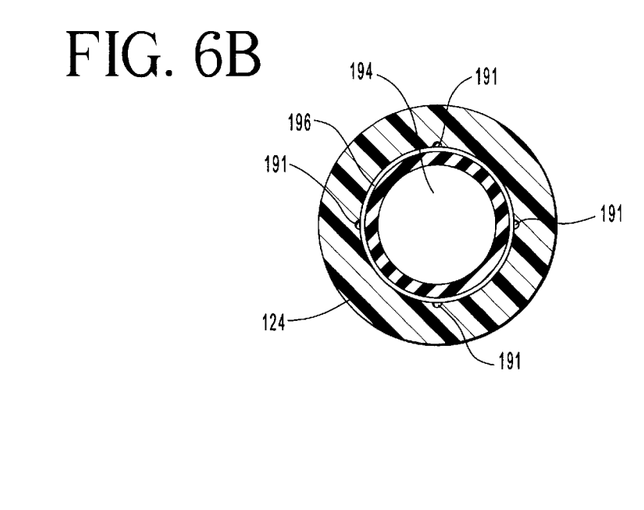
FIG. 6b is a cross sectional view of the housing illustrating the longitudinal housing vent grooves.

The distal end of dampening adaptor 190 has a partially hollowed piston 194. Preferably, dampening adaptor 190 and piston 194 are formed from a single mold, although they may be molded separately and connected by, for example, adhesive or sonic engagement. Sealingly fitted within the distal end of bore 192 and up against piston 194 is an air permeable, but liquid impermeable, plug 198 constructed of a low density polyethylene or similar material well known by those in the art. Carved out of dampening adaptor 190 adjacent to piston 194 are radial air vents 197 which permit air displaced from flashback chamber 166 during catheter insertion to exit dampening adaptor 190. As best illustrated in FIG. 6A, piston 194 has a plurality of circumferential wiper flanges 196. Wiper flanges 196 extend radially from piston 194 and contact housing cavity 122. Wiping flanges 196 create a sliding air seal against housing cavity 122 as piston 194 moves distally during needle retraction. As best illustrated in 6B, carved into housing cavity 122 are a plurality of longitudinal vent grooves 191. It will be appreciated by one skilled in the art that other designs which incorporate the general dampening theory may be designed. For example, rather than having longitudinal vent grooved 191 carved into housing cavity 122, similar units could be incorporated into piston 194.

In practice, the clinician first punctures the skin with introducer needle 160 and locates the patient's blood vessel. Once introducer needle 160 punctures the blood vessel, blood travels distally through introducer needle 160 displacing air through plug 198 and out radial vents 197. Once passed radial vents 197, air can exit housing 120 through the annular spaces between hub 162 and housing cavity 122, and out proximal housing aperture 128. The blood will eventually reach flashback chamber 166 alerting the clinician that the blood vessel has been successfully punctured and that introducer needle 160 should not be advanced further. Catheter housing 182 is then uncoupled from catheter adaptor 172 and catheter cannula 184 is advanced into the patient's blood vessel by sliding it along introducer needle 160.

While holding catheter 180 in place, the clinician depresses trigger 134, urging lock plate 136 downwardly and disengaging locking member 132. Consequently, spring 169 urges hub 162, and hence introducer needle 160, distally into housing cavity 122. As damping adaptor 190 moves distally from the force of spring 169, wiper flanges 196 create an air tight seal around piston 194. Ambient air in housing cavity 122 is compressed by piston 194 thereby dampening the velocity of introducer needle 160. Air is slowly expelled through longitudinal vent grooves 191, thus allowing introducer needle 160 to retract. As shown in FIG. 7, once introducer needle 160 is completely within housing cavity 122, the clinician secures catheter 180 to the patient and connects medication to catheter housing 182 where it is deposited directly into the patient's blood stream.

Figure 8:
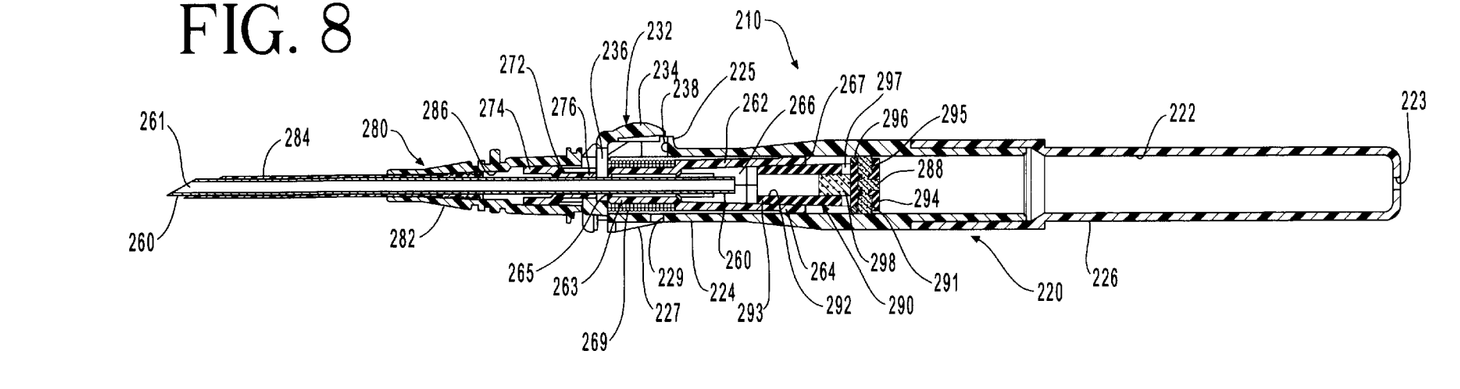
FIG. 8 is a longitudinal cross sectional view of the viscous material-filled piston dampening device embodiment of the present invention showing the introducer needle prior to retraction.
Figure 9:
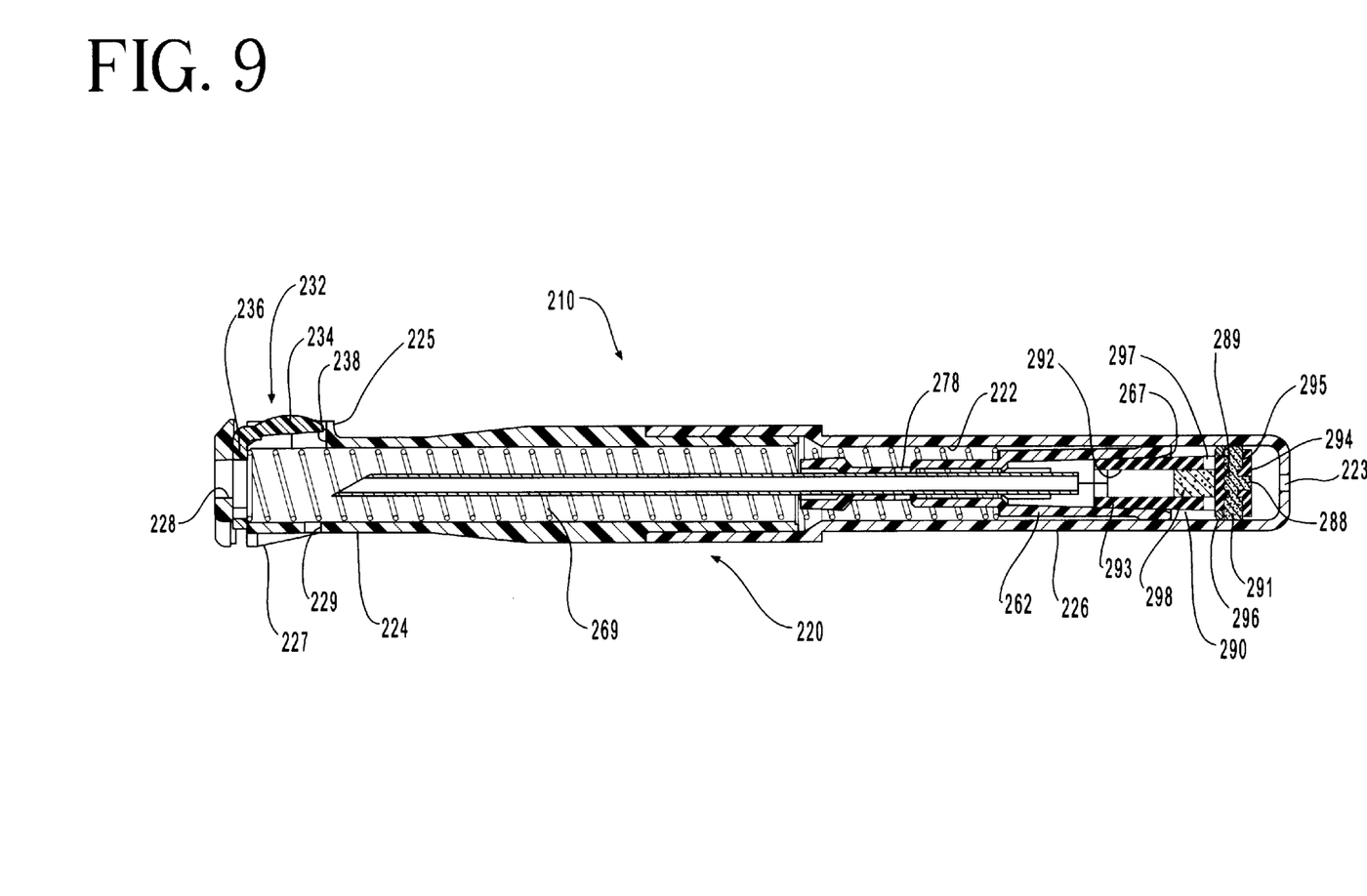
FIG. 9 is a longitudinal cross sectional view of the viscous material-filled piston dampening device embodiment of the present invention showing the introducer needle after retraction.

In a third embodiment the vascular access device operates in the same manner as described above except that a different dampening mechanism is used. Like parts are referred to by like numerals except that in this embodiment they begin with the number "2," indicating the part belongs to the third embodiment. As illustrated in FIGS. 8–9, the vascular access device 210 of the present invention has a dampening adaptor 290. Dampening adaptor 290 has a cylindrical interior bore 292, and a proximal dampening adaptor 293. The outer diameter of proximal dampening adaptor 293 is smaller than, and is sealingly received by, the larger inner diameter of distal hub opening 267, placing flashback chamber 266 and dampening adaptor 290 in fluid communication. Proximal dampening adaptor 293 is coupled to distal hub opening 267 by friction, adhesive or other engagement well known in the art.

Figure 8A:
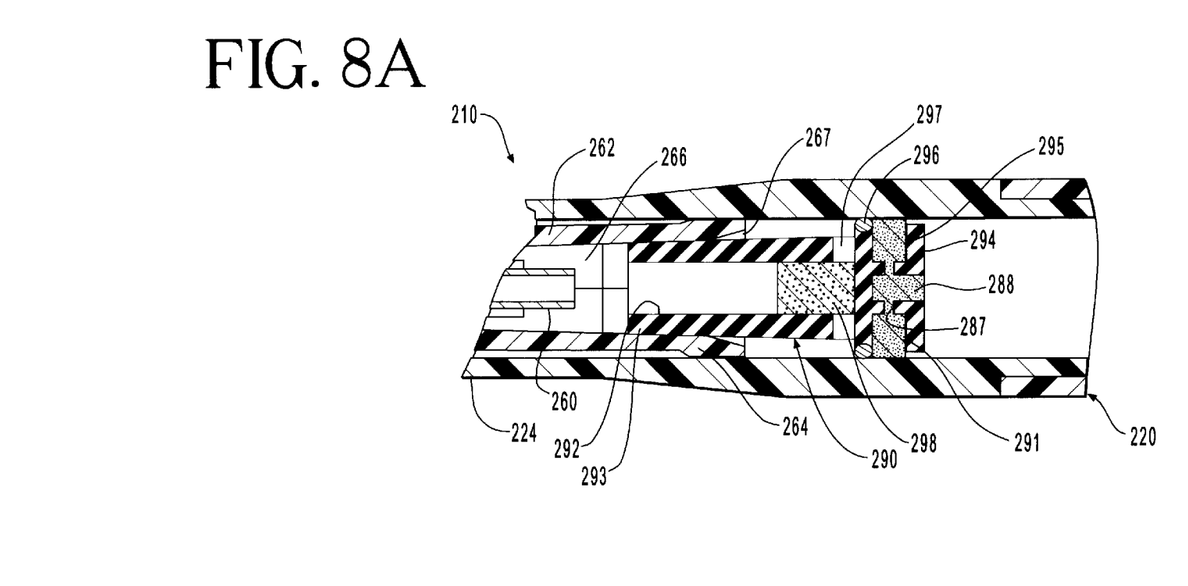
FIG. 8a is a longitudinal cross sectional view of the viscous material-filled piston.

The distal end of dampening adaptor 290 has a piston 294. Preferably, dampening adaptor 290 and piston 294 are formed from a single mold, although they may be molded separately and connected by, for example, adhesive engagement. Piston 294 has a circumferential groove 295. As best illustrated in FIG. 8A, piston 294 and circumferential groove 295 together define a piston hub 289. In turn, hub 289 has a center silicone port 288 and a plurality of radial silicone channels 287. After dampening adaptor 290 has been positioned within housing cavity 222, a high density silicone-based composition 291, or other viscous material, is injected into silicone port 288. Silicone 291 travels through radial silicone channels 287 until circumferential groove 295 is completely filled. The air displaced from circumferential groove 295 exits distally through an annular space between housing cavity 222 and the distal end of piston.

Proximately of circumferential groove 295, piston 294 has an o-ring 296 which creates a seal with inner housing cavity 222. 0-ring 296 ensures that silicone 291 does not leak from circumferential groove 295 as piston 294 travels distally through housing cavity 222. A second o-ring at the proximal end of piston 294 is generally not required because the force of piston 294 moving distally tends to keep silicone 288 within circumferential groove 295. However, depending on the assembly process or operation, a second o-ring may be placed distally of circumferential groove 295 so that silicone 291 does not leak out for whatever reason piston 294 is moved proximally. The friction caused by the additional o-ring against housing cavity 222 will also provide extra dampening. It will be appreciated that if a second o-ring is included, provisions, such as a pinhole, may be required to allow air in circumferential groove 295 to be displaced when silicone 291 is injected into silicone part 288.

Sealingly fitted in bore 292 and up against piston 294 is an air permeable, but liquid impermeable, plug 298 constructed of a low density polyethylene or similar material well known by those in the art. Carved out of dampening adaptor 290 and adjacent to piston 294 are radial air vents 297 which permit air displaced from flashback chamber 266 during catheter insertion to exit dampening adaptor 290.

In practice, the clinician first punctures the skin with introducer needle 260 and locates the patient's blood vessel. Once introducer needle 260 punctures the blood vessel, blood travels distally through introducer needle 260 displacing air through plug 298 and out radial vents 297. The blood will eventually reach flashback chamber 266 alerting the clinician that the blood vessel has been successfully punctured and that introducer needle 260 should not be advanced further. Catheter housing 282 is then uncoupled from catheter adaptor 272 and catheter cannula 284 is advanced into the patient's blood vessel by sliding it along introducer needle 260.

While holding catheter 280 in place, the clinician depresses trigger 234, urging lock plate 236 downwardly and disengaging locking member 232. Consequently, spring 269 urges hub 262, and hence introducer needle 260, distally into housing cavity 222. As damping adaptor 290 moves distally from the force of spring 269, the friction of silicone 291 and o-ring 296 against housing cavity 222 dampens the velocity and force with which introducer needle 260 is retracted. Depending on the size of housing vent 223, ambient air in housing cavity 222 is compressed providing additional dampening. As shown in FIG. 9, once introducer needle 260 is completely within housing cavity 222, the clinician secures catheter 280 to the patient and connects medication to catheter housing 282 where it is deposited directly into the patient's blood stream.

Figure 10:
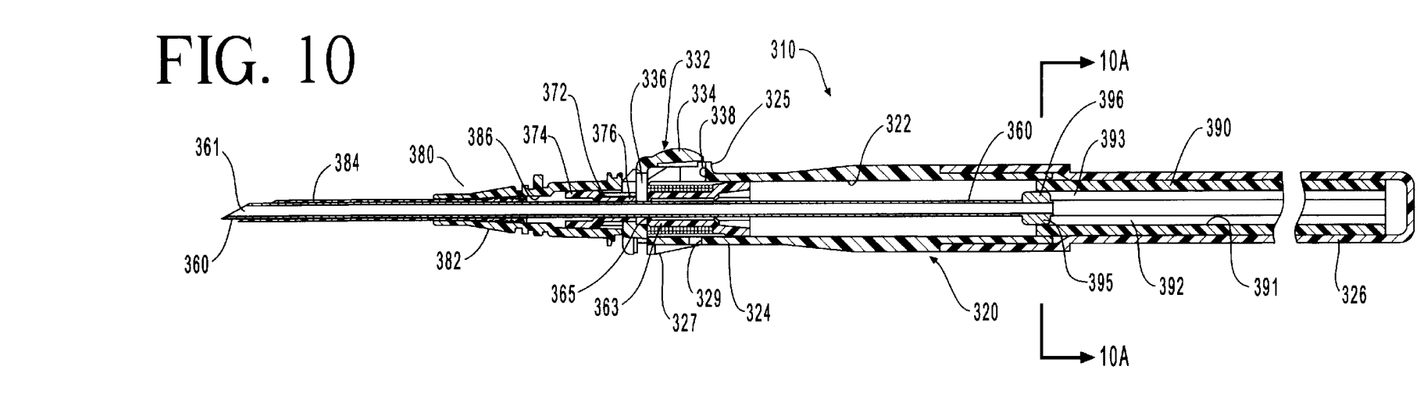
FIG. 10 is a longitudinal cross sectional view of the needle flange dampening device embodiment of the present invention showing the introducer needle prior to retraction.
Figure 10A:
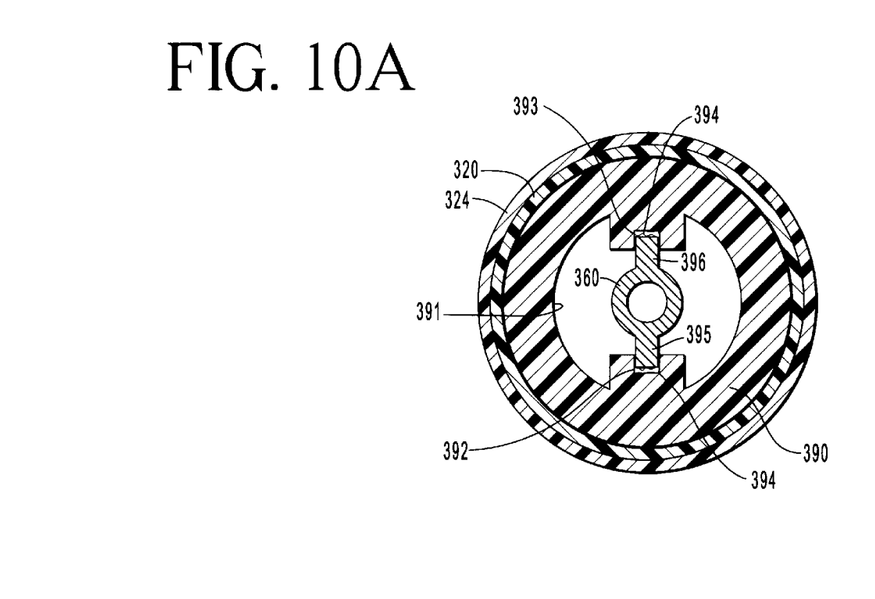
FIG. 10a is a cross sectional view of the dampening member showing the dampening tracks and the needle flanges.
Figure 11:
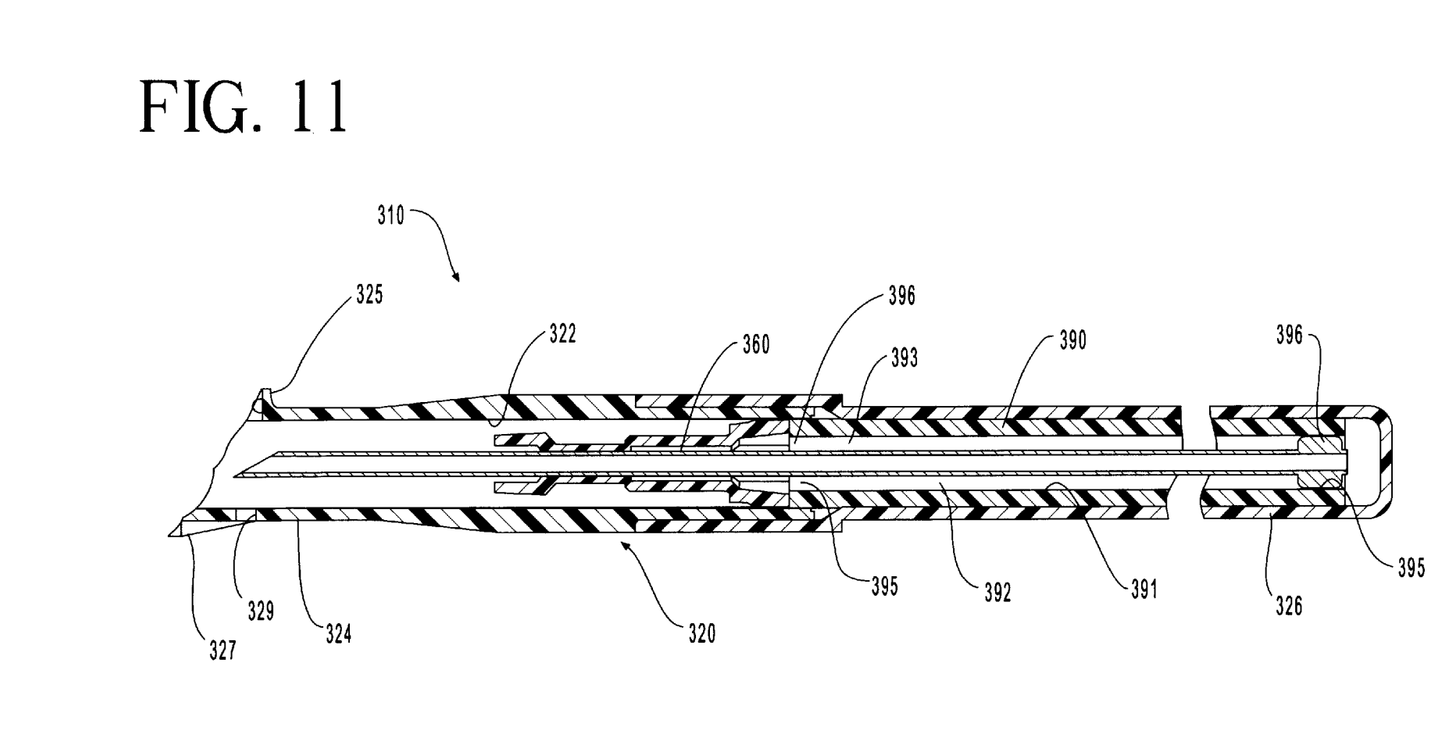
FIG. 11 is a longitudinal cross sectional view of the needle flange dampening device embodiment of the present invention showing the introducer needle after retraction.

In a fourth embodiment the vascular access device operates in the same manner as described above except that a different dampening mechanism is used. Like parts are referred to by like numerals except that in this embodiment they begin with the number "3." As illustrated in FIGS. 10–11, the vascular access device 310 has a generally hollow cylindrical dampening member 390 having an interior cavity 391. Dampening member 390 is positioned in distal housing 326. As best illustrated in FIG. 10A, running the entire length of interior cavity 391 are opposing tracks 392 and 393 which are at least partially filled with a high viscosity silicone 394 or other viscous material. With continued reference to FIG. 10A, the distal end of introducer needle 360 has a pair of opposing flanges 395 and 396 which are sized to fit within opposing tracks 392 and 393 of dampening member 390. Prior to needle retraction, the distal end of introducer needle 360 is partially recessed within dampening member 390.

In practice, the clinician first punctures the skin with introducer needle 360 and locates the patient's blood vessel. Once introducer needle 360 punctures the blood vessel, catheter housing 382 is then uncoupled from catheter adaptor 372 and catheter cannula 384 is advanced into the patient's blood vessel by sliding it along introducer needle 360. While holding catheter 380 in place, the clinician depresses trigger 334, urging lock plate 336 downwardly and disengaging locking member 332. Consequently, spring 369 urges hub 362, and hence introducer needle 360, distally into housing cavity 322. The velocity of introducer needle 360 is dampened by the friction of silicone 394 in tracks 392 and 393 with flanges 395 and 396. As shown in FIG. 11, once introducer needle 360 is completely within housing cavity 322, the clinician secures catheter 380 to the patient and connects medication to catheter housing 382 where it is deposited directly into the patient's blood stream.

Figure 12:
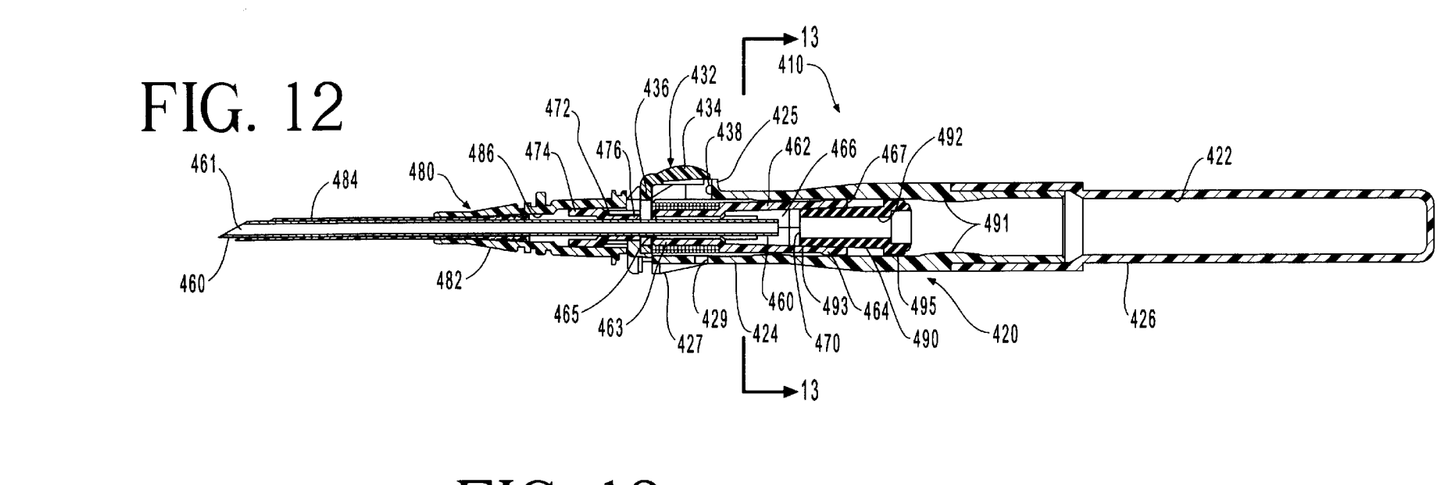
FIG. 12 is a longitudinal cross sectional view of the spring compression node dampening device embodiment of the present invention showing the introducer needle prior to retraction.
Figure 13:
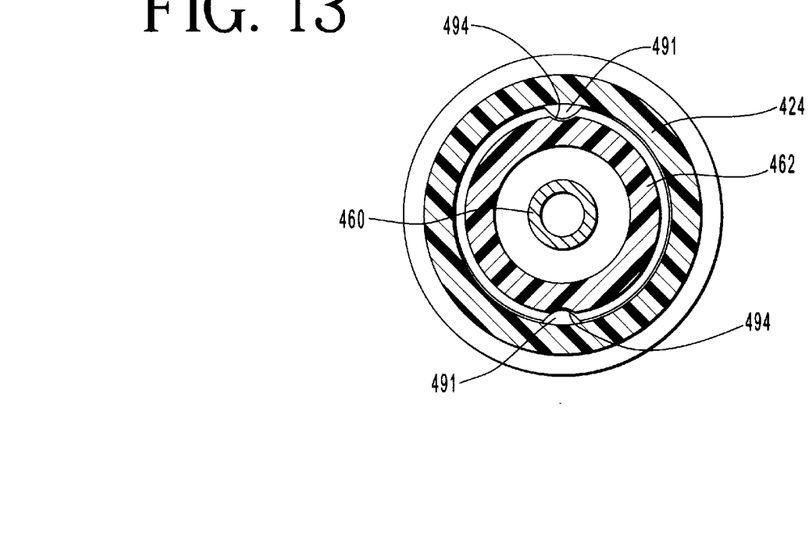
FIG. 13 is a cross sectional view taken along line 13—13 in FIG. 12.

In a fifth embodiment, the vascular access device operates in the same manner as described above except that a different dampening mechanism is used. Like parts are referred to by like numerals except that in this embodiment they begin with the number "4." As illustrated in FIGS. 12, the vascular access device 410 has a generally cylindrical housing 420 having an interior cavity 422. Disposed within housing cavity 422 is a generally cylindrical hollow hub 462. The interior cavity of hub 462 partially defines a flashback chamber 466. Hub 462 is sized such that it can travel the entire length of housing cavity 422. Prior to needle retraction, the proximal face of hub 462 is positioned near a proximal housing 424 and against a lock plate 436. Hub 462 additionally comprises a proximal hub 463 and a distal hub 464. Proximal hub 463 has a reduced diameter relative to distal hub 464. The disparity in relative diameters defines a hub shoulder 468. As best illustrated by FIG. 12, hub 462 also has a pair of longitudinal channels 494 running through distal hub 464. A damping adaptor 490, and more particularly guide ring 495, has a similar pair of longitudinal channels (not shown).

A coil spring 469, or similar resilient member, concentrically fits over introducer needle 460 and proximal hub 463. The diameter of spring 469 is greater than the diameter of proximal hub 463, but smaller than the diameter of distal hub 464. Prior to retraction, spring 469 is compressed between lock plate 436 and hub shoulder 468 of hub 462. Disposed within, or molded as part of, housing cavity 422, are a plurality of spring compression node 491. Spring compression nodes 491 are located distally of spring 469. As shown in FIG. 12, prior to needle retraction, some of the spring compression nodes 491 may reside within longitudinal channels 494 of distal hub 464. It will be appreciated by those skilled in the art that the number, position and size of compression nodes 491 may vary depending on the amount of dampening desired.

In practice, the clinician first punctures the skin with introducer needle 460 and locates the patient's blood vessel. Once introducer needle 460 punctures the blood vessel, blood travels distally through introducer needle 460 displacing air through plug 470. The blood will eventually reach the distal end of introducer needle 460 and exit into flashback chamber 466, alerting the clinician that the blood vessel has been successfully punctured and that introducer needle 460 should not be advanced further. Catheter housing 482 is then uncoupled from catheter adaptor 472 and catheter cannula 484 is advanced into the patient's blood vessel by sliding it along introducer needle 460.

While holding catheter 480 in place, the clinician depresses trigger 434 urging lock plate 436 downwardly and disengaging locking member 432. Consequently, spring 469 begins to elongate. The velocity of introducer needle 460 is dampened by spring compression nodes 491 which require that each individual coil of spring 469 radially contract before it can advance passed spring compression nodes 491 and continue through housing cavity 422. As each coil of spring 469 advances past spring compression node 491, hub 462, and hence introducer needle 460, is urged distally into housing cavity 422. Once introducer needle 460 is completely within housing cavity 422, the clinician secures catheter 480 to the patient and connects medication to catheter housing 482 where it is deposited directly into the patient's blood stream.

6. SUMMARY

After use, introducer needles are contaminated with the patient's blood and any blood borne diseases, such as HIV and hepatitis, the patient may carry. Exposed introducer needles, therefore, pose a health hazard to clinicians and other patients. To lessen the risk of accidental needle punctures or blood exposure, some vascular access devises are designed with spring retracting needles where the housing completely encloses the needle, protecting the clinician from accidental needle punctures.

While spring retracted needle designs significantly cut down on accidental needle punctures, some improvements to the designs could be made. For example, some blood will adhere to the needle through normal surface tension. Usually, this small amount of blood does not pose a threat to clinicians because it becomes enclosed by the housing. If the needle retracts too fast, however, blood on the needle may break the surface tension and splatter or drip on the patient or clinician. The potentially contaminated blood posses a serious health threat to the clinician and other medical personnel.

The present invention relates to dampening devices and methods that dampen the retraction velocity of needles used in connection with semi-automatic needle retracting vascular access devices. These devices prevent splattering or dripping of blood during needle retraction. In addition, the dampening devices of the present invention can be modified to regulate the amount of dampening and can be retrofit to existing vascular access devices.

What is claimed and desired to be secured by United States Letters Patent is:

1. A vascular access device comprising:
   a. a hollow housing having a distal end, a proximal end, and a cavity with a length;
   b. an introducer needle having a proximal end and a distal end;
   c. a hub in communication with the needle sized to travel the length of the housing cavity;
   d. a resilient member engaged with the hub, which applies a force and urges the needle in a distal direction;
   e. a locking member for releasably locking the needle in an extended position against the force of the resilient member;
   f. a dampening device located in the distal end of the cavity which generates air pressure during distal movement, the dampening device comprising an air vent for expelling pressurized air from the cavity and a piston disposed within the cavity, the piston including a circumferential groove and a viscous material disposed within the circumferential groove and in contact with the housing, wherein when the locking member is released, the force on the needle causes the needle to retract distally at a velocity, distal movement of the dampening device expels air from the vent and the velocity of the needle is dampened by distal movement of the dampening device and distal movement of the piston causes friction of the viscous material against the housing to dampen velocity of the needle.

2. The vascular access device of claim 1, wherein the piston further comprises at least one o-ring positioned on said piston to prevent the viscous material from leaking during needle retraction.

3. The vascular access device of claim 2, wherein the resilient member device is a spring.

* * * * *